United States Patent [19]

Igarashi et al.

[11] Patent Number: 5,583,160
[45] Date of Patent: Dec. 10, 1996

[54] METHYLSPHINGOSINE USED TO TREAT APOPTOSIS

[75] Inventors: Yasuyuki Igarashi; Sen-Itiroh Hakomori, both of Seattle, Wash.

[73] Assignee: The Biomembrane Institute, Seattle, Wash.

[21] Appl. No.: 357,306

[22] Filed: Dec. 14, 1994

Related U.S. Application Data

[63] Continuation-in-part of Ser. No. 965,614, Oct. 22, 1992, which is a continuation of Ser. No. 390,135, Aug. 7, 1989, abandoned, which is a continuation-in-part of Ser. No. 306,378, Feb. 3, 1989, abandoned.

[51] Int. Cl.$^6$ .......................... A61K 31/13; A61K 31/07; A61K 31/20

[52] U.S. Cl. .......................... 514/669; 514/725; 514/559; 514/114; 514/24

[58] Field of Search .................... 514/725, 559, 514/114, 24

[56] References Cited

U.S. PATENT DOCUMENTS 4,816,450   3/1989   Bell et al. .................................. 514/25

*Primary Examiner*—Theodore J. Criares
*Attorney, Agent, or Firm*—Sughrue, Mion, Zinn, Macpeak & Seas

[57] ABSTRACT

N-methylated sphingosine used to induce apoptosis.

5 Claims, 1 Drawing Sheet

5,583,160

METHYLSPHINGOSINE USED TO TREAT APOPTOSIS

Portions of the teachings disclosed herein were supported in part by a grant from the National Institutes of Health.

This application is a continuation-in-part of U.S. application Ser. No. 07/965,614 filed 22 Oct. 1992, pending, which is a continuation of U.S. application Ser. No. 07/390,135 filed 7 Aug. 1989, now abandoned, which is a continuation-in-part of U.S. application Ser. No. 07/306,378 filed 3 Feb. 1989, now abandoned.

BACKGROUND OF INVENTION

Glycosphingolipids (GSL's) are ubiquitous membrane components found in all animal cells and most plant cells, including yeasts. GSL's play crucial functional roles in cell-cell recognition, cell adhesion, and modulation of transmembrane signaling [1]. Patterns of GSL expression change dramatically during the processes of ontogenesis, oncogenesis and differentiation of stem cells into phenotypically terminal-stage cells. The knowledge of GSL distribution and expression was enriched greatly by introduction of the monoclonal antibody approach and many developmentally-regulated, tumor-associated GSL antigens have been identified on a chemical basis [2,3].

Apoptosis (programmed cell death) is a fundamental energy-dependent process in all multicellular organisms. Apoptosis helps control tissue size, shape and balance of cell number during morphogenesis, and plays an important role in oncogenic progression [4,5] and in other pathological processes such as reperfusion injury [6] and glomerulonephritis [7]. Aging neutrophils also have been shown to undergo apoptosis spontaneously [8,9]. Apoptotic senescent neutrophils are recognized and phagocytized by macrophages. The process has been suggested to represent a mechanism in vivo to limit neutrophil-mediated tissue injury at inflamed sites.

Various cytokines released during inflammation regulate the survival of neutrophils at the lesion either by promoting or by inhibiting cell death. Inflammatory mediators, such as endotoxic lipopolysaccharide, complement factor 5a and granulocyte-macrophage colony-stimulating factor, markedly inhibited neutrophil apoptosis [10]. In contrast, TNF-α, a potent neutrophil activator [11–13], has been shown to accelerate the rate of neutrophil apoptosis [14]. TNF-e responsive sphingomyelin hydrolysis and ceramide generation have been reported to be implicated in a signal transduction pathway that mediates induction of apoptosis by TNF-α in U-937 cells [15,16].

Calcium/phospholipid-dependent protein kinase (protein kinase C; PKC) is involved in intracellular signaling processing including those of cellular proliferation and differentiation in a variety of cells [17]. In hematopoietic cell systems, treatment with pharmacologic inhibitors of PKC causes the growth inhibition of both normal [18] and leukemic [19] progenitors. Several investigators reported that exposure to PKC inhibitors, such as H7 and staurosporine, induced apoptosis in HL-60 promyelocytic leukemia cells [20,21], MOLT-4 lymphoid leukemia cells and normal lymphocytes [22] and a variety of neoplastic cell lines [23]. In addition, activation of PKC by exposure to PMA prevented growth factor-deprived hematopoietic cells from undergoing apoptotic cell death [24]. Those observations suggest the potential role of PKC in the regulation of apoptosis.

Sphingosine, a sphingolipid breakdown product, has been shown to inhibit PKC in vitro and in cells [25–27]. Sphingosine and a catabolite thereof, DMS, had inhibitory effects on in vitro as well as in vitro tumor cell growth [28–30]. DMS also has an inhibitory effect on PKC activity as well as sphingosine [31].

Sphingosine and DMS appear to inhibit cell growth and exert a cytotoxic activity. It has been postulated that sphingosine functions as an endogenous modulator of PKC and plays important roles in cell growth, differentiation and oncogenesis [27,32]. However, because of difficulty of measuring changes in cellular sphingosine levels in response to biological stimuli, whether sphingosine functions physiologically in mediating biologic processes including growth suppression has not been determined [33].

On the other hand, human myeloid leukemia cell lines, including HL-60 cells, have retained the capacity to respond to inducers of differentiation with the cessation of growth and appearance of a more mature phenotype [34]. Recently, evidence of apoptosis has been described in HL-60 cells during both PMA-induced macrophage differentiation [35] and retinoic acid-induced neutrophilic differentiation [36].

However, it remains unclear what initiates apoptosis during cell differentiation. It is of interest to determine whether sphingosine, a potent endogenous PKC inhibitor, is involved in the mechanism of loss of proliferative capacity and induction of apoptosis during differentiation, since pharmacologic PKC inhibitors cause inhibition of cell growth and apoptosis.

SUMMARY OF THE INVENTION

The instant invention provides a means and method for inducing apoptosis in cells using as an active ingredient sphingosine or a methylated sphingosine.

DETAILED DESCRIPTION OF THE INVENTION

Figure 1B:
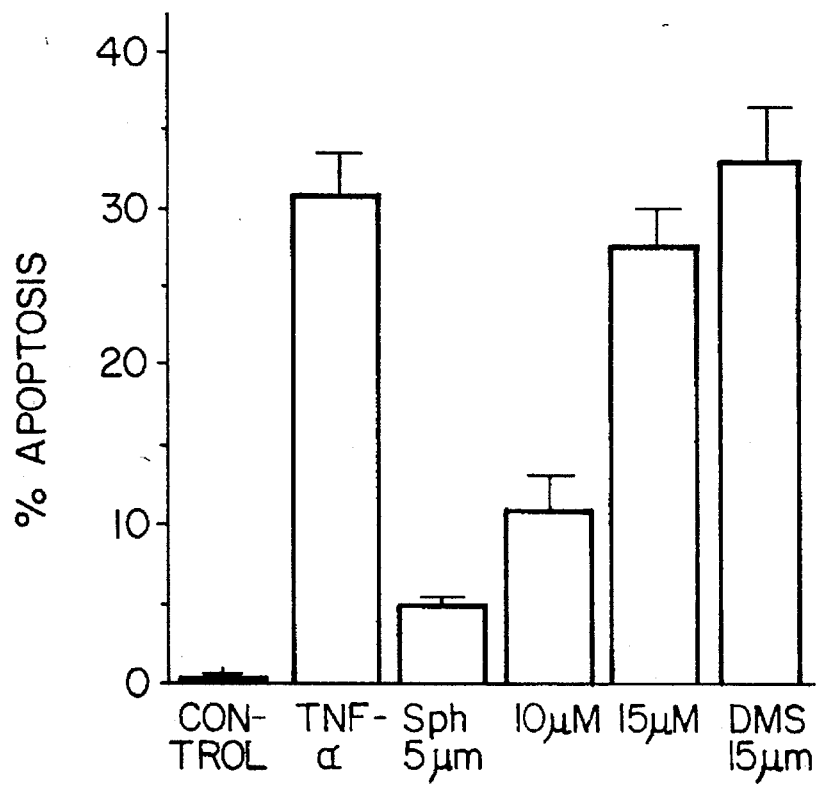
FIG. 1. (A) The percentage of apoptotic cells (assessed morphologically) of neutrophils treated for 6 h with an ethanol vehicle (Con), 3,000 U/ml TNF-α, 5, 10 and 15 μM sphingosine (Sph) and 15 μM DMS. (B) Time course of apoptosis of neutrophils incubated in the presence of an ethanol vehicle (hollow circles), 3,000 U/ml TNF-α (solid squares) or 15 μM sphingosine (solid circles). The values represent the average of three separate determinations (±S.E.).
Figure 1B:
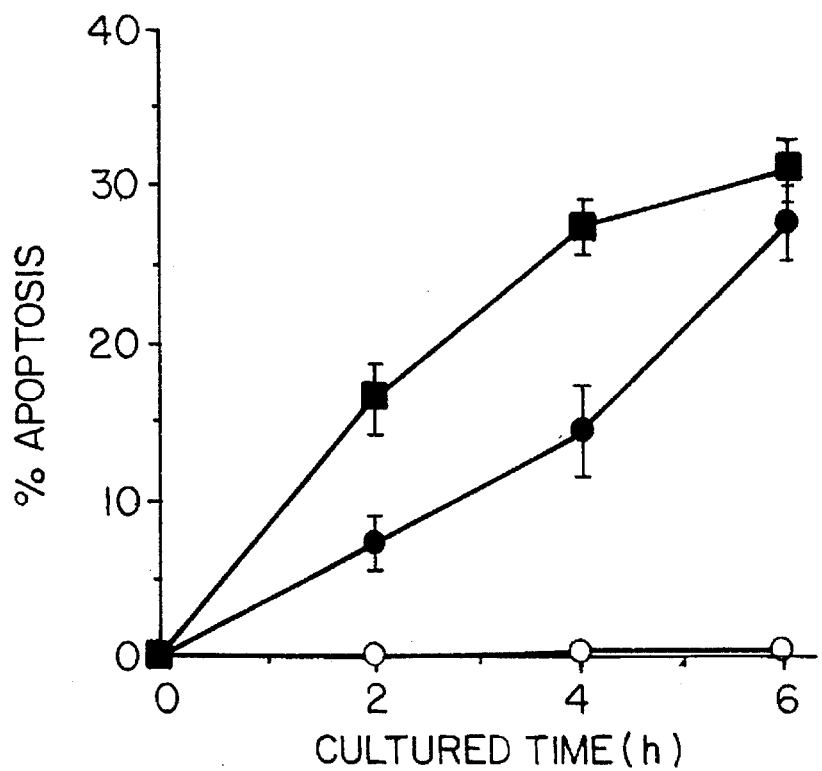

As used herein, "methylated sphingosine" is a sphingosine carrying one, two or three methyl groups at the nitrogen.

TNF-α has the capacity to induce or accelerate apoptosis of neutrophils as previously reported [14]. One physiologic function of TNF-α, which primes many neutrophil functions including the respiratory burst [11–13], may be the acceleration of apoptosis of primed neutrophils to limit neutrophil-mediated tissue injury. Previous studies demonstrated that TNF-α signaling involved sphingomyelin hydrolysis to ceramide by activation of sphingomyelinase [37,38]. In addition, treatment with exogenously added sphingomyelinase has been shown to cause an increase in concentration of sphingosine deacylated from ceramide, suggesting that sphingomyelinase and ceramidase functioned cooperatively [39].

Treatment of neutrophils with TNF-α results in an increase in cellular concentration of both ceramide and sphingosine. The increase of ceramide content was more rapid than that of sphingosine content. Thus, the increase of sphingosine content results from degradation of formed ceramide after TNF-α treatment.

Ceramide has been reported to initiate apoptosis [15,16]. A ceramide-activated protein kinase and phosphatase have been described in some cells [40–42], although whether those enzymes play a role in the mechanism of action of ceramide in mediating apoptotic signaling is unclear.

In neutrophils, sphingosine (5–15 μM), as well as TNF-α, are capable of inducing apoptosis. However, the same concentrations of ceramide or sphingosine-1-phosphate do not induce apoptosis.

Sphingosine inhibits PKC in vitro and in cells [25,27,43]. In addition, H7 and DMS, known as PKC inhibitors, also induce apoptosis. Induction of apoptosis by sphingosine may be related to inhibition of PKC activity.

On the other hand, sphingosine activates protein kinases distinct from PKC, cyclic nucleotide-activated kinases and calcium-dependent kinases, with high specificity for D-erythro-sphingosine [44], although whether sphingosine-dependent protein kinases are involved in processes of apoptosis is unclear.

An increase (8.6 pmol/$10^6$ cells) of sphingosine levels at 1 h after treatment with TNF-α is similar in magnitude to the transient increase in diacylglycerol that occurs on N-formyl-methionyl-leucyl-phenylalanine (fMLP) stimulation of neutrophils (about 6 pmol/$10^6$ cells) [45]. Moreover, the increase corresponds to that by exposure to about 10–20 μM sphingosine sufficient to induce apoptosis.

On the other hand, ceramide concentration is very high (about 200 μM) in unstimulated human neutrophils and the addition of exogenous cell permeable ceramide (C-8 ceramide, up to 20 μM) does not induce apoptosis of neutrophils incubated in medium containing 0.1% of BSA. Thus sphingosine deacylated from ceramide, not ceramide itself, may function as an endogenous modulator mediating induction of apoptosis by TNF-α in neutrophils.

Sphingosine and methylated derivatives thereof, such as monomethylsphingosine (MMS), show inhibitory effects on in vitro as well as in vivo tumor cell growth [29,30]. In most tumor cell types, DMS is a stronger inducer of apoptosis than sphingosine. DMS is detected in A431 epidermoid carcinoma cells [46] and murine IL2-dependent T lymphocyte CTLL cells [47].

Sphingosine and methylated derivatives thereof, such as DMS, induce apoptosis in leukemia cells such as the HL-60 human promyelocytic cell line. An exposure (2–6 h) to sphingosine or DMS is sufficient to cause DNA fragmentation and morphologic changes characteristic of apoptosis. Both sphingosine and DMS have an inhibitory effect on PKC activity [25-31]); and pharmacologic PKC inhibitors, such as H7 and staurosporine, also induce apoptosis. The induction of apoptosis by sphingosine and DMS may be related to inhibition of PKC activity. Induction of apoptosis by sphingosine and DMS, even in the presence of normal serum, was found in many tumor cell lines including CMK-7 megakaryocytic leukemia cells, Colo205 colon tumor cells and A431 epidermoid carcinoma cells.

The apoptotic capacity of PKC inhibitors including sphingosine and DMS may involve cell cycle-related factors [20]. For example, exposure of HL-60 cells to sphingosine resulted in down-regulation of c-myc gene expression which plays an important role in regulation of both cell proliferation and apoptosis [48]. HL-60 cell differentiation towards macrophages also has been shown to be associated with the down-regulation of c-myc mRNA [49].

A further possibility is that PKC inhibitors may affect the cell cycle by inhibiting topoisomerase II, since topoisomerase II is phosphorylated and activated by PKC [50]. In fact, topoisomerase II inhibitors, as well as PKC inhibitors, strongly induce apoptosis in HL-60 cells [20].

On the other hand, sphingosine and DMS also have been known to regulate a number of biologic processes including growth suppression in PKC-independent pathways [33]. Chao et al. [51] reported that sphingosine induced-dephosphorylation of the Rb gene product, and the effect of sphingosine on Rb, was independent of inhibition of PKC. The potent and specific activation of Rb by sphingosine correlated with inhibition of cell growth and with arrest at the $G_0/G_1$ phase of the cell cycle. In addition, sphingosine activates protein kinases, which were distinct form PKC, cyclic nucleotide-activated kinases, and calcium-dependent kinases, with high specificity for D-erythro-sphingosine [44].

Exogenously added sphingosine is metabolized to ceramide and sphingosine-1-phosphate, and a progressive conversion from sphingosine to sphingomyelin or ceramide monohexoside (CMH) is observed [52]. Although ceramide, S-1-P and CMH failed to cause DNA fragmentation in HL-60 cells, sphingomyelin hydrolysis and ceramide generation have been reported to be implicated in a signal transduction pathway that mediates induction of apoptosis by TNF-α in U-937 cells [15,16]. Ceramide has no effect on PKC activity [53].

Although apoptotic DNA fragmentation is detected first after treatment for 10 h with 4β-phorbol 12-myristate 13-acetate (PMA), cellular levels of sphingosine increase 3 h after PMA treatment and thereafter increase concomitantly with the proportion of apoptotic cells. In contrast, in apoptotic cells induced by H-7, there is no increase observed in sphingosine content after 6 h. Taken together the fact that exogenously-added sphingosine could induce the apoptosis of the cells, those observations suggest that sphingosine may function as an endogenous inducer of apoptosis occurring in differentiated cells, and that the sphingosine increase might not be the simple result of apoptosis or cell death.

Sphingosine is produced from ceramide by ceramidase in cells. Cellular ceramide is thought to be formed by the acylation of de novo biosynthesized dihydrosphingosine, followed by desaturation [54-56] or by the hydrolysis of sphingomyelin in response to stimulation with agents such as TNF-α and γ-interferon [57]. Treatment with PMA causes no hydrolysis of sphingomyelin. Increase of sphingosine levels in HL-60 cells differentiated by the treatment with PMA may be due to changes in activity of ceramidase or biosynthesis of sphingolipids during cell differentiation. [$^3$H]$C_6$-ceramide added exogenously in HL-60 cells and macrophage differentiation derivatives thereof were metabolized rapidly to sphingosine, CMH and sphingomyelin. Differentiated HL-60 cells exhibit a markedly increased conversion of [$^3$H] ceramide sphingosine, suggesting elevated ceramidase activity in the cells. In contrast, the conversion of [$^3$H] ceramide to sphingomyelin in differentiated HL-60 cells is less than 50% of that in untreated cells. The decrease of sphingomyelin synthesis from ceramide in differentiated HL-60 cells may result in decreased formation of diacylglycerol, an endogenous PKC activator [58] since sphingomyelin is synthesized by phosphatidylcholine:ceramide phosphocholine transferase (sphingomyelin synthase), which transfers the phosphorylcholine head group from the phospholipid phosphatidylcholine to ceramide, yielding sphingomyelin and diacylglycerol.

Apoptosis is an essential physiologic process which helps regulate cell numbers in normal as well as tumor tissues. If the rate of apoptosis is enhanced in tumor cells, total tumor mass will decrease. That is a potentially useful approach for antitumor therapy. DMS, a strong inducer of apoptosis, inhibits tumor growth [29].

Hiraishi et al. [59] reported a close correlation between $Le^y$ expression (defined by mAb BM1) and apoptosis in various tumor tissues and normal epithelial tissues. Apoptosis was accessed not only by typical morphologic features (for example, shrinkage of cytoplasm or condensation of nucleus) but also by nick-end labeling for detection of DNA fragmentation [60]. Some important findings from that study were: (i) apoptotic cells were detected frequently in $Le^y$-positive cell populations but not in $Le^y$-negative populations; (ii) cells that were $Le^y$-positive were usually PCNA (proliferating cell nuclear antigen)-negative, nick-end labeling positive and showed apoptotic morphology; and (iii) apoptotic morphology was not correlated strongly with positive staining for Fas antigen (CD95/Apo-1). Those trends were observed in normal and tumor tissues from esophagus, colon and stomach, and in normal thymus.

$Le^y$ antigen is known to be present in both GSL's and glycoproteins, particularly those having mucin-type domains [61,62]. Some structures of $Le^y$ GSL are:

A correlation between apoptosis and Gb3/CD77 expressions in B cell populations was demonstrated first by a morphologic study employing electron micrography [63]. The fact that Gb3/CD77 functions as a receptor for Shiga toxin [64] and verotoxin (VT) [65] suggests that toxin-dependent killing of Gb3/CD77(+) cells may depend on apoptosis. A recent study showed that the B-subunit of VT (VT-B) which causes binding of VT to Gb3/CD77, also induces apoptosis in Gb3/CD77(+) B cells.

Gb3 glycolipid, when bound to VT-B, is internalized and creates a- signal to induce DNA fragmentation [66]. Furthermore, when Gb3/CD77(+) cells are treated with VT-B, a Gb3/VT-B complex accumulates at the nuclear membrane.

Sphingosine can be obtained from commercial sources, such as Sigma Chemical Company (St. Louis, Mo.) or Aldrich Chemical Company (Milwaukee,. Wis.). Alternatively, sphingosine can be synthesized as known in the art, for example, see Igarashi et al. (1989) [28] or EP 0381514.

N-methylated sphingosines such as, monomethyl sphingosine and dimethyl sphingosine, also can be synthesized as taught in EP 0381514.

For some of the studies disclosed herein, other compounds, such as sphingosine-1-phosphate and ceramides are synthesized as known in the art, see, for example, U.S. Pat. No. 5,260,288, Igarashi et al. (1989) [28], Vunnam & Radin (1979) [67] or Ruan et al. (1992) [68]. Other ceramides can be made by acylation of sphingosine as taught in Van Veldhoven et al. (1989) [69].

Other ceramides, sphingomyelin, glucosylceramide (ceramide monohexoside, CMH), phorbol myristate acetate

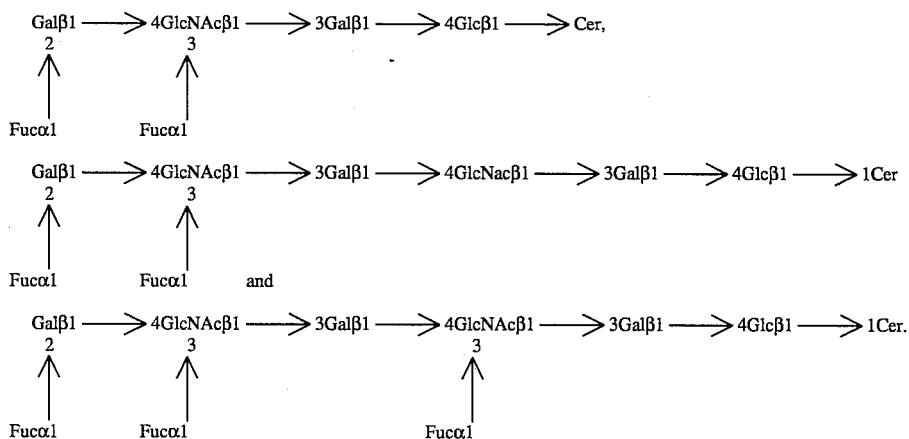

It is believed that only $Le^y$ GSL (not $Le^y$ glycoprotein) antigen is involved in apoptosis and possibly by one or more of the three $Le^y$ GSL structures provided hereinabove. During differentiation, an $Le^y$ structure may define the stage of cells committed to apoptosis.

Globotriaosylceramide (Gb3) is expressed highly in Burkitt lymphoma and was long known as "Burkitt lymphoma antigen" (BLA) before being chemically identified as:

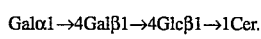

BLA also is expressed highly in certain B cell populations (where it has been termed recently as "CD77") particularly in germinal centers of tonsils and other lymphoid tissues which exhibit active apoptosis. It has been detected at lower levels in a variety of other cells and tissues. Gb3 also is abundant in individuals of histo-blood group pK (a rare phenotype seen in about 0.01% of most populations).

(PMA), staurosporine, propidium iodide (PI) and H7 can be purchased commercially, for example, from Sigma and Calbiochem (San Diego, Calif.). Other reagents, such as acetic anhydride, chloroform methanol and the like are available commercially. Radiolabelled compounds are available, for example from ICI (Irvine, Calif.) and NEN (Boston, Mass.). Thin layer chromatography (TLC) plates are available, for example, from EM Separations (Gibbstown, N.J.). Natural human TNF-α can be obtained, for example, from Otsuka Cellular Technology Int. (Tokushima, Japan). Ribonuclease A and bovine serum albumin can be obtained from a variety of sources, such as, Life Technologies (Gaithersburg, Md.) and Sigma.

Cell lines, such as the human promyelocytic leukemia HL-60 cells (American Type Culture Collection, Rockville, Md.) can be grown as known in the art, as in RPMI 1640 medium containing 10% heat-inactivated fetal bovine serum supplemented with 100 units/ml penicillin, 100 µg/ml streptomycin and 2 mML-glutamine. The cells are treated, for example, with various sphingolipids or PKC inhibitors, for 6 h at 37° C. and then presence of apoptotic cells, is ascertained, for example by determining amount of DNA fragmentation. All sphingolipids generally are dissolved in ethanol. Control experiments can be performed with ethanol (<0.1%) as the vehicle. Cell differentiation into macrophages can be induced in the cells with 5 nM PMA. Adherent cells are recoverable, for example, by scraping with a cell scraper after removing nonadherent cells. For DNA fragmentation and lipid analyses, adherent cells and nonadherent cells can be combined and harvested.

Heparinized venous blood for isolation of leukocytes can be obtained from volunteers. Leukocytes can be isolated, for example, by dextran sedimentation and centrifugation on a Ficoll-Paque (Pharmacia LKB, Uppsala, Sweden) cushion, as previously described [70]. Contaminating erythrocytes can be removed by hypotonic lysis with the remaining cells being resuspended in a suitable medium, such as, RPMI 1640 containing 0.1% BSA. Such processing generally yields >98% viable leukocytes, as determined by Wright-Giemsa staining.

To determine ceramide and sphingosine concentration, lipids are extracted from cells. For ceramide measurement, lipid extracts can be incubated with *Escherichia coli* diacylglycerol kinase as, previously reported [71]. Ceramide phosphate then is isolated by TLC and the ceramide mass can be quantified. Sphingosine concentrations can be measured by conversion to N-[$^3$H] acetylated sphingosine by acylation with [$^3$H] acetic anhydride [72]. After lipid extracts are treated with 0.1N NaOH for 1 h, dried samples are dissolved in 40 µl of 0.008N NaOH in methanol/10 mM solution of [$^3$H] acetic anhydride (1/1). Acylation proceeds for 1 h at 37° C. Following treatment of samples with NaOH, N-[$^3$H] acetylated sphingosine is isolated by TLC and the sphingosine mass is quantified by, for example, autoradiography with counting in a scintillation counter. Dihydrosphingosine is present in low amounts and generally is not significant [54-56,73].

DNA fragmentation can be analyzed, for example, by using agarose gel electrophoresis [20]. About 5×10$^6$ neutrophils are harvested, washed and incubated in 0.5 ml of 50 mM Tris-HCl, ph 8.0, containing 1 mM EDTA, 0.25% Nonidet P-40 (Sigma) and 0.1% ribonuclease-A at 37° C. for 30 min. About 50 µl of 10 mg/ml proteinase-K (Boehringer, Mannheim, Germany) then is added and the incubation continued for an additional 30 min. After incubation, 0.1 ml of leading buffer (0.25% bromophenol blue-0.25% xylene cyanol FF-30% glycerol) is added to the sample. About 25 µl of the tube contents are loaded into each well of an agarose gel, such as about a 2% gel, and electrophoresis is carried out at about 10 V/cm. A Hae III Digest of φX174 DNA (New England Biolabs, Inc., Beverly, Mass.) is applied to each gel to provide size markers of 1,353, 1,078, 872, 603, 310 bp, respectively. The DNA in gels is visualized under ultraviolet light after staining with ethidium bromide (Sigma).

For morphologic assessments of apoptosis in cells, cytocentrifuge slides are prepared and stained with Wright-Giemsa stain. Cells are examined under oil immersion light microscopy and apoptotic cells are assessed. Apoptosis can be identified in cells containing one or more darkly stained pyknotic nuclei cell shrinkage and formation of membrane blots and apoptic bodies. [8,10]. For assessment of the percentage of cells showing morphology of apoptosis, about 500 cells/slide can be counted. Viability by trypan blue exclusion also can be assessed.

Apoptosis of cells can be assessed by flow cytometry as previously reported (74). A 200×g centrifuged cell pellet (1×10$^6$ cells) is suspended in 1 ml of hypotonic fluorochrome solution (50 µg/ml PI, 0.1% sodium citrate, 0.1% Triton x-100). The samples are placed overnight in the dark at 4° C. and then the fluorescence of individual nuclei is measured using, for example, an EPICS flow cytometer (Coulter Co., Hialeah, Fla.). The data can be analyzed using the compatible COULTER flow cytometry software (Coulter).

For Northern blots, total cellular RNA is collected by, for example, the method of Chomczynski and Sacchi [75]. Poly (A)$^+$RNA is isolated using commercially available mRNA purification kits such as from Pharmacia Biotech, Piscataway, N.J., separated on a 1% agarose/2.2M formaldehyde gel and transferred to a nylon-membrane filter (Amersham Co., Arlington Heights, Ill.). Blots are hybridized for 16 h at 42° C. to appropriate [$^{32}$P]-labeled DNA probes. After hybridization, the filters are washed twice with, for example, 2×SSC (20×SSC is 3M NaCl, 0.3M sodium citrate, pH 7.0) and 0.1% SDS at room temperature for 10 min followed by one washing with 0.2×SSC and 0.1% SDS at 42° C. for 30 min. The blot is visualized by, for example, autoradiography.

Sphingosine and N-methylated derivatives thereof, and preferably dimethylsphingosine (DMS), can be used to induce apoptosis in certain cell populations. Hence a target biologic preparation is exposed to an amount of sphingosine or N-methylated derivative thereof which induces apoptosis. A biological preparation is a cell-containing composition, such as a cell suspension, for example, cell lines or a blood; tissue, for example, culture of explants or biopsy specimens; organs, for example those for transplantation and those for an ex vivo treatment; or an organism.

In vitro, sphingosine or N-methylated derivatives thereof can be added to the culture medium or holding medium. A suitable final concentration, as discernable from the teachings provided herein, is 10–20 µM. The active ingredient(s) can be provided suspended in a biologically compatible medium, preferably, a liquid medium, such as a tissue culture fluid or a physiologic saline or other means, such as contained within liposomes. A plurality of types of sphingosines can be used wherein the aggregate concentration is as noted hereinabove.

For other applications, the sphingosines of the instant invention can be combined with physiologically compatible buffers, carriers or diluents which would enable suitable administration, such as orally or parenterally, by implant or depot, within microcapsules such as liposomes, and other known delivery means. The composition may contain other industry known additives such as bulking agents, emulsifiers, preservatives, binders, fillers and the like, which are directed to the suitability of the administered product. The art of preparing such administered formulations is well-settled. The amounts administered are determinable based on plasma half-life, bioavailability and other pharmakinetic studies, as known in the art, and fall within the range of concentrations recited hereinabove. The artisan can refer to any of a variety of pharmacology and pharmaceutic textbooks for art-recognized methods and products, such as, "Remington's".

A suitable delivery means is by the use of microencapsulated active agents, such as by use of liposomes. There are many art-recognized means for preparing liposomes, such as, taught in Park et al., Cancer Res., 54:2213–2217, 1994. For example, a phosphatidylcholine, cholesterol and sphingosines are mixed, dried, hydrated and sonicated or extruded to form liposomes.

The instant invention now will be exemplified further in the following non-limiting examples.

EXAMPLES

Example 1

Sphingosine, N-octanoylsphingosine (C8ceramide), sphingosine-1-phosphate and DMS were synthesized as described previously [28,67-68]. All sphingolipids were dissolved in ethanol. Control experiments were performed with ethanol (<0.1%) as the vehicle. H7 was obtained from Calbiochem-Novabiochem Co. (San Diego, Calif.). Natural human TNF-α ($5\times10^7$ U/mg) was obtained from Otsuka Cellular Technology Int. (Tokushima, Japan). Ribonuclease-A and bovine serum albumin (BSA, essentially fatty acid-free) were obtained from Sigma Chemical Co. (St. Louis, Mo.). [$^3$H] Acetic anhydride was from DuPont-New England Nuclear (Boston, Mass.). HPLC-grade chloroform and methanol and thin-layer chromatography (TLC) plates were from EM Separations (Gibbstown, N.J.). Autoradiography enhancer spray, Resolution TLC™, was from L.M. Corp. (Chestnut Hill, Mass.).

Heparinized venous blood was obtained from healthy volunteers. Neutrophils were isolated by dextran sedimentation and centrifugation on a Ficoll-Paque (Pharmacia LKB, Uppsala, Sweden) cushion as previously described [70]. After contaminating erythrocytes were removed by hypotonic lysis, cells were resuspended with RPMI 1640 containing 0.1% BSA. Such processing yielded >98% viable neutrophils, as determined by Wright-Giemsa staining.

Purified neutrophils ($5\times10^6$/ml) were treated with human TNF-α (3,000 U/ml) for varying times and then lipids were extracted from cells. For ceramide measurement, lipid extracts were incubated with Escherichia coli diacylglycerol kinase as previously reported [71]. Ceramide phosphate then was isolated by TLC and the ceramide mass was quantified. Sphingosine concentrations were measured by conversion to N-[$^3$H] acetylated sphingosine by acylation with [$^3$H] acetic anhydride [72]. After lipid extracts were treated with 0.1N NaOH for 1 h, dried samples were dissolved in 40 µl of a 1:1 solution of 0.008N NaOH in methanol and 10 mM [$^3$H] acetic anhydride. Acylation proceeded for 1 h at 37° C. Following treatment of samples with NaOH, N-[$^3$H] acetylated sphingosine was isolated by TLC and the sphingosine mass was quantified.

DNA fragmentation was analyzed by agarose gel electrophoresis [20]. About $5\times10^6$ neutrophils were harvested, washed and incubated in 0.5 ml of 50 mM Tris-HCl, ph 8.0, containing 1 mM EDTA, 0.25% Nonidet P-40 (Sigma) and 0.1% ribonuclease-A at 37° C. for 30 min. About 50 µl of 10 mg/ml proteinase-K (Boehringer, Mannheim, Germany) then was added and the incubation continued for an additional 30 min. After incubation, 0.1 ml of loading buffer (0.25% bromophenol blue-0.25% xylene cyanol FF-30% glycerol) was added. About 25 µl of the tube contents were loaded into each well of 2% agarose gels and electrophoresis was carried out at 10 V/cm. A Hae III digest of φX174 DNA (New England Biolabs, Inc., Beverly, Mass.) was applied to each gel to provide size markers. The DNA in gels was visualized under ultraviolet light after staining with ethidium bromide (Sigma).

For morphologic assessments, neutrophils ($5\times10^6$/ml) treated with the different agents were applied to cytocentrifuge slides and stained with Wright-Giemsa stain. Cells were examined under oil immersion light microscopy and apoptotic neutrophils were defined as cells containing one or more darkly stained pyknotic nuclei [8,10]. For assessment of the percentage of cells showing morphology of apoptosis, 500 cells/slide were counted. Viability by trypan blue exclusion also was assessed.

The cellular concentration of ceramide increased by 68% (from 189±42 to 317±15 pmol/$10^6$ cells) at 5 min after the addition of TNF-α (3,000 U/ml). Ceramide concentrations in neutrophils incubated at 37° C. in the absence of TNF-α were unchanged.

Under the same conditions, TNF-α induced an increase in sphingosine content. Sphingosine concentrations increased by 95% (from 9.1±0.2 to 17.7±3.4 pmol/$10^6$) at 1 h after the addition of TNF-α. The increase occurred continuously over 1 h. Sphingosine concentrations in neutrophils incubated at 37° C. for 1 h in the absence of TNF-α increased by only 29% (from 9.1±0.2 to 11.8±1.7 pmol/$10^6$ cells).

Thus, treatment of neutrophils with TNF-α caused an increase of both ceramide and sphingosine concentrations.

As previously reported [14], agarose gel electrophoresis of DNA from neutrophils treated for 6 h with TNF-α (3,000 U/ml) showed DNA fragmentation with a pattern characteristic of internucleosomal fragmentation. DNA from neutrophils treated with an ethanol vehicle, cell-permeable C8-ceramide (15 µM) or sphingosine-1-phosphate (15 µM) was unfragmented. However, sphingosine (15 µM), as well as H7 (50 µM) and DMS (15 µM), caused internucleosomal DNA fragmentation. The effects of sphingosine were detected first after 2 h and increased with longer treatment.

Induction of apoptosis by TNF-α had been confirmed previously by ultrastructural examination [14]. Light microscopy of neutrophils treated for 6 h with TNF-α (3,000 U/ml) or sphingosine (15 µM) provided many neutrophils with morphologic features of apoptosis, such as one or more darkly stained pyknotic nuclei and cytoplasm vacuolation. There was no evidence of significant necrotic cell death (assessed by the ability of neutrophils to exclude trypan blue) in culture.

Isolated neutrophils have been known to undergo apoptosis spontaneously [8–10]. The percentage of apoptotic cells in neutrophils treated with an ethanol vehicle increased from 0±0 to 1.1±0.5% over 6 h. The percentages of apoptosis in neutrophils treated for 6 h with TNF-α (3,000 U/ml), sphingosine (15 µM) DMS (15 µM) and H7 (50 µM) were 31.1±3.3, 27.7±3.0, 33.1±4.1 and 27.6±3.0%, respectively. Treatment with sphingosine induced apoptosis in a dose-dependent manner. The time course study showed that the proportion of neutrophils demonstrating morphologic features of apoptosis increased progressively with time after addition of TNF-α (3,000 U/ml) or sphingosine (15 µM).

Example 2

Sphingosine, DMS, sphingosine-1-phosphate, C8-ceramide and [$^3$H] sphingosine (specific activity 88 mCi/mmol) were synthesized as described previously [28,67,68,76]. [$^3$H] sphingosine was converted to [$^3$H]C6-ceramide by acylation with hexanoic anhydride as reported previously [69] and purified by high. performance TLC. Ceramide (type III; from bovine brain), sphingomyelin (from bovine brain), glucosylceramide (ceramide monohexoside, CMH; from human Gaucher's spleen), PMA, staurosporine and PI were obtained from Sigma Chemical Co. (St. Louis, Mo.). H7 was from Calbiochem-Novabiochem Co. (San Diego, Calif.). [$^3$H] Acetic anhydride (specific activity 50 mCi/mmol) was from New England Nuclear (Boston, Mass.). HPLC-grade chloroform and methanol and TLC plates were from EM Separations (Gibbstown, N.J.). Autoradiography enhancer spray, Resolution TLC™, was from L.M. Corp. (Chestnut Hill, Mass.).

The human prolyelocytic leukemia HL-60 cells (American Type Culture Collection, Rockville, Md.) were grown in RPMI 1640 medium containing 10% heat-inactivated fetal bovine serum supplemented with 100 units/ml penicillin, 100 μg/ml streptomycin and 2 mM L-glutamine. The cells were treated with various sphingolipids or PKC inhibitors for 6 h at 37° C. and then DNA fragmentation was analyzed. All sphingolipids were dissolved in ethanol. Control experiments were performed with ethanol (<0.1%) as the vehicle. Cell differentiation towards macrophages was induced in the cells with 5 nM PMA. Adherent cells were recovered by scraping with a cell scraper after removing nonadherent cells. For DNA fragmentation and lipid analyses, adherent cells and nonadherent cells were combined and harvested.

DNA fragmentation was analyzed by using agarose gel electrophoresis [20]. About $5 \times 10^6$ HL-60 cells were harvested, washed and incubated in 0.5 ml of 50 mM Tris-HCl, pH 8.0, containing 1 mM EDTA, 0.25% Nonidet P-40 (Sigma) and 0.1% ribonUclease-A (Sigma) at 37° C. for 30 min. About 50 μl of 10 mg/ml proteinase-K (Boehringer, Mannheim, Germany) then was added and the incubation continued for an additional 30 min. After incubation, 0.1 ml of loading buffer (0.25% bromophenol blue 0.25% xylene cyanol FF-30% glycerol) was added. About 25 μl of the tube content were loaded into each well of 2% agarose gels and electrophoresis was carried out at 10 V/cm. A Hae III digest of φX174 DNA (New England Biolabs, Inc., Beverly, Mass.). The DNA in gels was visualized under ultraviolet light after staining with ethidium bromide (Sigma).

For morphologic assessments, HL-60 cells were washed after treatment with different agents and cytocentrifuge slides were prepared and stained with Wright-Giemsa stain. Apoptotic cells were identified by morphologic features characteristic of apoptosis (e.g., cell shrinkage, nuclear condensation and formation of membrane blots and apoptotic bodies) on stained cell preparations.

Apoptosis of HL-60 cells treated with different agents was measured by flow cytometry as previously reported [74]. The 200×g centrifuged cell pellet ($1 \times 10^6$ cells) was suspended in 1 ml of hypotonic fluorochrome solution (50 μg/ml PI, 0.1% sodium citrate, 0.1% Triton x-100). The samples were placed overnight in the dark at 4° C. and then the fluorescence of individual nuclei was measured using an EPICS flow cytometer (Coulter Co., Hialeah, Fla.). The data were analyzed using COULTER flow cytometry software (Coulter).

The cellular concentrations of sphingosine were measured as previously reported [72]. The assay is based on quantitative conversion of sphingosine to [$^3$H]C$_2$-ceramide by acylation with [$^3$H] acetic anhydride. Briefly, $1 \times 10^7$ cells were harvested and pelleted by centrifugation. Three ml of chloroform/methanol (1/2, v/v) were added and mixed thoroughly. Phases were separated by adding 2 ml each of chloroform and 1M NaCl. Three ml of 0.2N NaOH in methanol were added to the lower chloroform phase followed by incubation at room temperature for 1 h. After phases were separated by adding 3 ml each of chloroform and 1M NaCl, samples from the lower chloroform phase were evaporated under N$_2$. Dried samples were dissolved in 40 μl of 0.008N NaOH in redistilled methanol/10 mM solution of [$^3$H] acetic anhydride (1/1) by sonication. Acylation proceeded for 1 h at 37° C. Following treatment of samples with NaOH, samples were chromatographed on TLC plates using chloroform/methanol/7N N$_4$OH/water (80/20/0.5/0.5) as the developing solvent and exposed to Kodak X-Omat film at −80° C. Radioactive spots corresponding to [$^3$H]C$_2$-ceramide were scraped and counted in a liquid scintillation counter. The assay is directed to quantification of sphingosine but measures both sphingosine and dihydrosphingosine (an intermediate in the de novo pathway of sphingolipid biosynthesis). Nevertheless, dihydrosphingosine most likely would be present in much smaller amounts than sphingosine [54–56, 73].

About $1 \times 10^6$ cells were pelleted by centrifugation and resuspended in 0.8 ml of 0.9% (w/v) NaCl. Then, 3 ml of chloroform/methanol (1/2) were added and mixed thoroughly. Phases were separated by adding 1 ml each of chloroform and 1M NaCl and phospholipid content in the lower chloroform phase was estimated by the method of Ames and Dubin [77].

The metabolism of exogenously added [$^3$H]C$_6$-ceramide (a short chain, cell-permeable analog of ceramide) in HL-60 cells was compared with that in similar macrophage differentiation derivatives induced by treatment with PMA for 48 h. About $1 \times 10^7$ cells were harvested, washed and resuspended in 1 ml of RPMI 1640 medium containing 10% heat-inactivated fetal bovine serum and 3 μM [$^3$H]C$_6$-ceramide. After incubation at 37° C. for various periods, cellular lipids were extracted by the method of Bligh and Dyer [78]. Samples from the chloroform phase were dried, dissolved in 40 μl of chloroform/methanol (2/1) and then spotted on TLC plates. Plates were developed with chloroform/methanol/28%NH$_4$OH (80/20/2) or chloroform/methanol/acetic acid/water (100/60/20/5). The bands were visualized and identified under ultraviolet light by staining the control lipids with primulin. After spraying with Resolution TLC™, autoradiography was performed with Kodak X-Omat film at −80° C. Radioactive spots corresponding to sphingosine, sphingomyelin or CMH were scraped and counted in a liquid scintillation counter.

Total cellular RNA was collected by the method of Chomczynski and Sacchi [75]. Poly (A)$^+$RNA was isolated by an mRNA purification kit (Pharmacia Biotech, Piscataway, N.J.), separated on a 1% agarose/2.2M formaldehyde gel and transferred to a nylon membrane filter (Amersham Co., Arlington Heights, Ill.). Blots were hybridized for 16 h at 42° C. to the following [$^{32}$P]-labeled DNA probes: (i) the 1.4 kbp ClaI/EcoRI fragment of the c-myc DNA representing exon 3 generated from the plasmid pHSR-1 [79]; and (ii) the β-actin DNA generated by PCR previously described [80]. After hybridization, the filters were washed twice with 2×SSC (20×SSC is 3M NaCl, 0.3M sodium citrate, pH 7.0) and 0.1% SDS at room temperature for 10 min followed by one washing with 0.2×SSC and 0.1% SDS at 42° C. for 30 min.

DNA agarose gel electrophoresis revealed that a 6 h exposure of HL-60 cells to sphingosine caused DNA fragmentation with a pattern characteristic of internucleosomal fragmentation as well as pharmacologic inhibitors of PKC, such as H7 or staurosporine. DNA from cells treated with an ethanol vehicle for 6 h was unfragmented. Increases in sphingosine concentrations resulted in increased DNA fragmentation. The effect of sphingosine (10 μM) was detected first after 2 h and increased with longer treatment.

Exogenously added sphingosine is converted to other sphingolipids such as ceramide and sphingosine-1-phosphate in cells [52]. To evaluate the specificity of action of sphingosine, HL-60 cells were treated with various sphingolipids. Treatment for 6 h with cell-permeable C$_8$-ceramide (10 μM), sphingosine-1-phosphate (10 μM) or CMH (10 μM) failed to cause DNA fragmentation. However, exposure to DMS (10 μM) induced internucleosomal DNA fragmentation.

The appearance of morphologic features characteristic of apoptotic cell death was monitored in HL-60 cells treated with sphingosine (10 μM), H7 (50 μM) and DMS (10 μM) for 6 h. The ethanol vehicle had no effect on HL-60 cells. Cells treated with sphingosine revealed an abundance of apoptotic cells in culture, which were characterized by stereotypic morphologic changes of apoptosis, such as cell shrinkage, condensed chromatin and fragmented nuclei. Exposure to H7 and DMS induced more prominent apoptotic changes than did Sphingosine. On the other hand, exposure to sphingosine, H7 or DMS did not induce cellular differentiation towards macrophages or neutrophils.

After treatment of HL-60 cells with different agents, the percentage of apoptotic cells was measured by a flow cytometric method. The reduced DNA content of apoptotic cells resulted in an unequivocal hypodiploid DNA peak which was discernible from the diploid DNA peak. Although treatment of HL-60 cells with an ethanol vehicle did not induce apoptosis, an apparent hypodiploid DNA peak of apoptotic cells was detected in cultures treated with sphingosine (10 μM), H7 (50 μM) and DMS (10 μM). The percentages of apoptotic cells in cultures treated with an ethanol vehicle, sphingosine (10 μM), H7 (50 μM) and DMS (10 μM) were 1.1±0.2, 55.6±7.8, 72.8±10.5 and 84.2±11.6%, respectively. Exposure to DMS (10 μM) caused larger percentages of apoptotic cells than did that to sphingosine (10 μM).

As previously described [35], internucleosomal DNA fragmentation occurred during PMA-induced differentiation into macrophages. When HL-60 cells were cultured with 5 nM PMA, the cells were induced to differentiate into macrophage-like adherent cells showing prominent pseudopods. Internucleosomal DNA fragmentation was detected first after treatment for 10 h with PMA and increased with longer treatment. There was no detectable DNA fragmentation in untreated HL-60 cells. Cells with characteristic features of apoptosis were observed during PMA-induced differentiation by light microscopy. In addition, differentiated HL-60 cells into macrophages were seen to engulf apoptotic cells. Moreover, the flow cytometric analysis revealed that the percentages of apoptotic cells were 1.9, 5.0, 8.6 and 9.4% after treatment with PMA for 3, 10, 24 and 48 h, respectively.

Cellular concentrations of sphingosine, which functions as an inducer of apoptosis, were measured in HL-60 cells induced to differentiate by treatment with PMA for various times. To correct for possible losses during extraction, mass levels of sphingosine, which partitions in membranes, were expressed as molar percentages of phospholipids. The phospholipid levels were unchanged during PMA-induced cell differentiation. The sphingosine level in untreated HL-60 cells was 0.0394±0.0078 mol %/phospholipid (6.5±0.4 pmol/$10^6$). Sphingosine levels in the cells increased concomitantly with an increasing proportion of apoptotic cells during cell differentiation. The sphingosine level in differentiated HL-60 cells after a 48 hr exposure to PMA was about 3.3-fold greater than that in untreated cells. On the other hand, the level of sphingosine in H-7 treated apoptotic cells (percentage of apoptotic cells was 73% at 50 μM, after 6 h incubation) did not show any increase. Namely, sphingosine content of control and H-7 treated cells was 6.0 and 5.5 pmol/$10^6$ cells, respectively.

Sphingosine and complex sphingolipids such as sphingomyelin and glycosphingolipids are formed from ceramide [54–56]. To evaluate the alteration between sphingolipid metabolism in HL-60 cells and that in the macrophage-like differentiation induced derivatives, cell-permeable [$^3$H]C$_6$-ceramide was added to the cell suspension and the metabolism thereof was examined. [$^3$H]C$_6$-ceramide was metabolized rapidly to [$^3$H]sphingosine, [$^3$H]CMH and [$^3$H]sphingomyelin. Formation of sphingosine and CMH in HL-60 cells differentiated by treatment for 48 h with PMA markedly increased as compared to that in untreated cells. In contrast, at each time point, sphingomyelin formation in differentiated HL-60 cells was less than 50% of that in untreated cells.

HL-60 cells have been reported to overexpress the c-myc protooncogene [81]. Overexpression of c-myc may play an essential role in maintaining the high proliferative rate of HL-60 cells. The down-regulation of mRNA for c-myc has been shown to be related to induction of apoptosis [82].

The effects of sphingosine on c-myc expression were examined. The c-myc gene was expressed constitutively in HL-60 cells and exposure to sphingosine resulted in down-regulation of c-myc mRNA that was detected as early as 1 h. Sphingosine (10 μM) was capable of c-myc down-regulation by 60–70% at 4 h.

Example 3

Cell lines were obtained from the ATCC and cultured as recommended. In cultures where the effect of serum was investigated, cultures were maintained in serum-free conditions, that is, the same culture medium but without bovine serum.

Then cultures of three various cells were exposed to 20 μM or 10 μM of the agents noted in Tables I and II. The degree of apoptosis induced was assessed.

In the studies, cancer cells were more susceptible to the apoptosis inducing effect of the sphingosines. Thus normal cell lines HUVEC and A31 were more refractory and showed less apoptosis. When cells acclimated to growth under serum-free conditions, in HL1 medium, were tested, HUVEC and A31 cells, as well as some of the cancer cells presented with an elevated susceptibility to apoptosis induction by the sphingosines. However, whether in the presence of serum or not, ceramides did not induce apoptosis.

Those data indicate that the threshold for apoptosis induction in transformed cells is lower than in normal cells. Either a different mechanism is operable in cancer cells or entry to apoptosis is dependent on the stage of the cell cycle and the relatively unregulated or higher growth rate of transformed cells brings a greater number of cells sooner to the requisite cell cycle stage for apoptosis induction.

Example 4

Egg phospatidylcholine, cholesterol and DMS in physiologic saline are mixed in a ratio of 4.5:4.5:1, the mixture is evaporated and is treated to produce liposomes (Kraft & Anderson, Nature 301: 621, 1983; Igarashi et al., Biochemistry 28: 6796, 1989).

Mice were injected subcutaneously with the metastatic and invasive BL6 cell line (Hart et al., Amer. J. Path. 97: 587, 1979; Poote et al., Canc. Res. 42: 2770, 1982) with 1×$10^5$ cells in 0.05 ml of Dulbecco-modified Eagle's medium.

The mice are injected intravenously with the DMS liposomes (control animals receive liposomes with saline only) and injections are repeated on days 5, 10, 15, 20, 25 and 30.

The primary tumor is excised on day 21 and lung colonization is assessed on day 35. Tumor development and colony development are determined. Tumor development and colony development are reduced in the experimental group.

TABLE I

DEGREE OF APOPTOSIS IN VARIOUS CELLS*

| Cell Line | S-1-P** | Spn | DMS | TMS | C2Cer | C6Cer | C8Cer |
|---|---|---|---|---|---|---|---|
| CMK-7[1] | −*** | +++++ | ++++ | − | − | − | − |
| HL60 | ++ | ++++ | +++++ | +++ | − | − | − |
| U937 | − | ++ | + | − | − | − | − |
| B16 | −/+ | ++ | + | −/+ | −/+ | − | − |
| HT29 | ++ | −/+ | ++ | −/+ | −/+ | −/+ | − |
| HRT18 | ND | + | +++ | −/+ | − | − | − |
| A431 | ND | ++ | +++ | −/+ | − | − | − |
| MKN74[1] | − | ++ | +++ | − | − | −/+ | − |
| COLO205 | −/+ | +++ | +++ | − | − | −/+ | − |
| A31 | − | − | + | − | − | −/+ | − |
| HUVEC | −/+ | −/+ | − | − | − | − | − |
| CMK-7[+] | + | +++++ | ++++ | ++ | −/+ | − | − |
| HL60[+] | − | ++++ | ++++ | + | + | − | − |
| U937[+] | ND | −/+ | + | ND | ++ | + | ND |
| RPMI[2] | ND | + | −/+ | ND | − | − | ND |
| RPMI > HL1[2] | ND | −/+ | + | ND | +++ | −/+ | ND |
| HL1[2] | ND | −/+ | + | ND | ++ | + | ND |

*Cells were treated with 20 μM of the various agents for 6 hours.
**S-1-P is sphingosine-1-phosphate; Spn is sphinsone; DMS is dimethylsphingosine; TMS is trimethylsphingosine; and C2Cer, C6Cer and C8Cer are ceramides having amide linked groups of 2, 6 and 8 carbon atom length.
***
−/+ < 10%
+ 10–25%
ND Not done
++ 25–45%
+++ 45–65%
++++ 65–85%
+++++ > 85%
[+]Grown under serum-free conditions in HL1 medium (Ventrex) containing growth factors suitable for hematopoietic cells.
[1]CMK-7 cells are described in Sato et al., Br. J. Hemat. 72: 184–190 (1989) and MKN74 cells are described in Motoyama et al. Acta Med. Biol. 27: 49–63 (1979).
[2]The three entries depict controls using U937 cells maintained in RPMI medium only, HL1 medium only and in a culture maintained in RPMI for the first half of the culture and then switched into HL1 medium (RPMI > HL1).

TABLE II

DEGREE OF APOPTOSIS in VARIOUS CELLS*

| Cell Line | S-1-P | Spn | DMS | TMS | C2Cer | C6Cer | C8Cer |
|---|---|---|---|---|---|---|---|
| CMK-7 | ++ | +++++ | ++++ | −/+ | − | + | − |
| CMK-7 (SF) | + | +++++ | ++++ | ND | +++ | ++ | + |
| HL60 | − | +++ | +++ | ++++ | − | + | − |
| HL60 (SF) | −/+ | +++ | ++++ | − | ++++ | ++ | −/+ |
| U937 | − | ++ | +++ | − | − | −/+ | − |
| U937 (SF) | + | + | + | ND | +++ | ++ | ND |

*Cells were treated with 10 μM of the various agents for 18 hours.

REFERENCES

1. Hakomori, S. J. Biol. Chem. 265: 18713–18716 (1990).
2. Hakomori, S., Adv. Cancer Res. 52: 257–331 (1989).
3. Hakomori, S. & Kannagi, R., J. Natl. Cancer Inst. 71:231–251 (1983).
4. Arends, M. J. & Wyllie, A. H., Int. Rev. Exp. Pathol. 32:223–254 (1991).
5. Wyllie, A. H., In: Bowen, I. D. and Lockshin, R. A. (eds.), Cell death in biology and pathology, pp. 9–34. London, Chapman & Hall (1981).
6. Gottlieb, R. A. et al., J. Clin. Invest. 94: 1621–1628 (1994).
7. Baker, A. J. et al., J. Clin. Invest. 94: 2105–2116 (1994).
8. Savill, J. S. et al., J. Clin. Invest. 83:865–875 (1989).
9. Sayill, J. et al., Nature 343: 170–173 (1990).
10. Lee, A. et al., J. Leukoc. Biol. 54: 283–288 (1993).
11. Shalaby, M. R. et al., J. Immunol. 135: 2069–2073 (1985).
12. Gamble, J. R. et al., Proc. Natl. Acad. Sci. USA. 82: 8667–8671 (1985).
13. Schleiffenbaum, B. & Fehr, J. J. Clin. Invest. 86: 184–195 (1990).
14. Takeda, Y. et al., Int. Immunol. 5: 691–694 (1993).
15. Obeid, L. M. et al., Science 259: 1769–1771 (1993).
16. Jarvis, W. D. et al., Proc. Natl. Acad. Sci. USA 91: 73–77 (1994).

17. Nishizuka, Y., JAMA 262:1826–1833 (1989).
18. Katayama, N. et al., Blood 73:123–130 (1989).
19. Tohda, S. et al., Leukemia 5:813–814 (1991).
20. Gorczyca, W. et al., Cancer Res. 53:3186–3192 (1993).
21. Jarvis, W. D. et al., Cancer Res. 54: 1707–1714 (1994).
22. Traganos, E. et al., Int. J. Oncol. 2: 47–59 (1993).
23. Bertrand, R. et al., Proc. Am. Assoc. Cancer Res. 34:1735 (1993).
24. Gerschenson, L. E. & Rotello, R. J. FASEB J. 6: 2450–2455 (1992).
25. Hannun, Y. A. et al., J. Biol. Chem. 261: 12604–12609 (1986).
26. Merrill, A. H., Jr. et al., J. Biol. Chem. 261: 12610–12615 (1986).
27. Hannun, Y. A. & Bell, R. M., Science 243: 500–507 (1989).
28. Igarashi, Y. et al., Biochemistry 28: 6796–6800 (1989).
29. Endo, K. et al., Cancer Res. 51: 1613–1618 (1991).
30. Okoshi, H. et al., Cancer Res. 51: 6019–6024 (1991).
31. Khan, W. A. et al., Biochem. Biophys. Res. Comm. 172: 683–691 (1990).
32. Hakomori, S., J. Biol. Chem. 265: 18713–18716 (1990).
33. Hannun, Y. A. & Linardic, C.M. Biochem. Biophys. Acta 1154:223–236 (1993).
34. Koeffler, H. P., Blood 62:709–721 (1983).
35. Gunji, H. et al., J. Clin. Invest. 89: 954–960 (1992).
36. Martin, S. J. et al., Clin. Exp. Immunol. 79: 448–453 (1990)
37. Dressier, K. A. et al., Science 27: 1715–1718 (1992).
38. Heller, R. A. & Kronke, M., J. Cell Biol. 126:5–9 (1994).
39. Slife, C. W. et al., J. Biol. Chem. 264: 10371–10377 (1989).
40. Mathias, S. et al., Proc. Natl. Acad. Sci. USA 88: 10009–10013 (1991).
41. Lozano, J. et al., J. Biol. Chem. 269: 19200–19202 (1994).
42. Dobrowsky, R. T. & Hannun, Y. A. Adv. Lipid Res. 25:91–104 (1993).
43. Hannun, Y. A. et al., J. Biol. Chem. 261: 12604–12609 (1986).
44. Pushkareva, M. Y. et al., J. Biol Chem. 267: 15246–15251 (1992).
45. Honeycutt, P. J. & Niedel, J. E. J. Biol. Chem. 261:15900–15905 (1986).
46. Igarashi, Y. et al., J. Biol. Chem. 265: 5385–5389 (1990).
47. Felding-Habermann, B. et al., Biochemistry 29: 6314–6322 (1990).
48. Evan, G. J. et al., Cell 69:119–128 (1992).
49. Bernstein, S. H. et al., FEBS Lett. 294: 73–76 (1991).
50. Sahyoun, N. et al., Proc. Natl. Acad. Sci. USA 83:1603–1607 (1986).
51. Chao, R. et al., J. Biol. Chem. 267:23459–23462 (1992).
52. Sadahira, Y. et al., Proc. Natl. Acad. Sci. USA 89:9686–9690 (1992).
53. Merrill, A. H., Jr. et al., Biochemistry 28: 3138–3145 (1989).
54. Merrill, A. H., Jr. & Wang, E., J. Biol. Chem. 261:3764–3769 (1986).
55. Rother, J. et al., Biochem. Biophys. Res. Comm. 189:14–20 (1992).
56. van Echten, G. & Standhoff, K., J. Biol. Chem. 286: 5341–5344, (1993).
57. Kim, M. -Y. et al., J. Biol. Chem. 266: 484–489 (1991).
58. Hannun, Y. A., Science 246:1050 (1989).
59. Hiraishi, K. et al., Glycobiology 381–390 (1993).
60. Gavrieli, Y. et al., J. Cell Biol. 119:493–501 (1992).
61. Abe, K. et al., J. Biol. Chem. 258: 11793–11797 (1983).
62. Nudelman, E.D. et al., J. Biol. Chem. 261: 11247–11253 (1986).
63. Mangeney, M. et al., Eur. J. Immunol. 21: 1131–1140 (1991).
64. Jacewicz, M. et al., J. Exp. Med. 163: 1391–1404 (1986).
65. Lingwood, C. A. et al., J. Biol. Chem. 262: 8834–8839 (1987).
66. Mangeney, M. et al., Cancer Res. 53: 5314–5319 (1993).
67. Vunnam, R. R. & Radin, N. S., Biochim. Biophys. Acta 573: 73–82, (1979).
68. Ruan, F. et al., Bioorg. Med. Chem. Lett. 973–978 (1992).
69. Van Veldhoven, P. P. et al., Anal. Bioahem. 183: 177–189 (1989).
70. Kimura, S. et Biochem. Pharmacol. 44: 1585–1595 (1992).
71. Okazaki, T. et al. , J. Biol. Chem. 265: 15823–15831 (1990).
72. Ohta, H. et al., Anal. Biochem. 222: 489–494 (1994).
73. Lavie, Y. et al., Biochim. Biophys. Acta 1220: 323–328 (1994).
74. Nicoletti, I. et al., J. Immunol. Methods 139: 271–279 (1991).
75. Chomczynski, P. & Sacchi, N., Anal. Biochem. 162: 156–159 (1987).
76. Toyokuni, T. et al., J. Labelled Comp. Radiopharm. 29: 567–574 (1991).
77. Ames, B. & Dubin, D. T., J. Biol. Chem. 235: 769–775 (1960).
78. Bligh, E.G. & Dyer, W. J., Can. J. Biochem. Physiol. 37:911–917 (1959).
79. Alitalo, K. et al., Proc. Natl. Acad. Sci. USA 80: 1707–1711 (1983).
80. Goodman, R.E. et al., J. Immunol. 1.52:5189–5198 (1994).
81. Bertrand, R. et al., Cancer Res. 51: 6280–6285 (1991).
82. Alnemri, E. S. et al., Cancer Res. 52: 491–495 (1992).

All references cited are incorporated herein in entirety.

The artisan will recognize that various changes and modifications can be made to the instant invention without departing from the spirit and scope thereof.

We claim:

1. A method for inducing apoptosis comprising:

(a) exposing cells to N-methylated sphingosine in an amount sufficient to induce apoptosis; and (b) maintaining said cells in the presence of N-methylated sphingosine until a predetermined level of cell death has occurred.

2. The method of claim 1, wherein said N-methylated derivative is dimethyl sphingosine.

3. The method of claim 1, wherein said N-methylated sphingosine is contained in a liposome.

4. The method of claim 1, wherein said amount is 10–20 µM.

5. The method of claim 1, wherein said N-methylated sphingosine is suspended in a biologically compatible liquid.

* * * * *